United States Patent
Segawa

(10) Patent No.: US 7,938,774 B2
(45) Date of Patent: May 10, 2011

(54) ENDOSCOPE APPARATUS HAVING CONTROLLED HEATER

(75) Inventor: Kazunori Segawa, Hachioji (JP)

(73) Assignee: Olympus Medical Systems Corporation, Tokyo (JP)

( * ) Notice: Subject to any disclaimer, the term of this patent is extended or adjusted under 35 U.S.C. 154(b) by 975 days.

(21) Appl. No.: 11/646,160

(22) Filed: Dec. 27, 2006

(65) Prior Publication Data

US 2007/0149856 A1   Jun. 28, 2007

(30) Foreign Application Priority Data

Dec. 27, 2005   (JP) ................... 2005-376237

(51) Int. Cl.
*A61B 1/00*   (2006.01)
*A61B 1/04*   (2006.01)

(52) U.S. Cl. ........................ 600/169; 600/103

(58) Field of Classification Search .................. 600/103, 600/109, 117, 118, 160, 169, 176, 178, 180, 600/182, 412, 474

See application file for complete search history.

(56) References Cited

U.S. PATENT DOCUMENTS

| | | | | |
|---|---|---|---|---|
| 4,076,018 A | * | 2/1978 | Heckele | 600/168 |
| 4,402,311 A | * | 9/1983 | Hattori | 600/117 |
| 4,484,823 A | | 11/1984 | Peuker | |
| 4,884,557 A | * | 12/1989 | Takehana et al. | 600/145 |
| 5,402,769 A | * | 4/1995 | Tsuji | 600/109 |
| 5,419,312 A | * | 5/1995 | Arenberg et al. | 600/108 |
| 5,448,990 A | * | 9/1995 | De Faria-Correa | 600/129 |
| 5,536,236 A | | 7/1996 | Yabe et al. | |
| 5,605,532 A | | 2/1997 | Schermerhorn | |
| 5,647,840 A | * | 7/1997 | D'Amelio et al. | 600/169 |
| 5,845,634 A | * | 12/1998 | Parker | 128/200.26 |
| 6,235,027 B1 | * | 5/2001 | Herzon | 606/51 |
| 6,468,204 B2 | * | 10/2002 | Sendai et al. | 600/160 |
| 6,796,939 B1 | * | 9/2004 | Hirata et al. | 600/179 |
| 6,853,879 B2 | * | 2/2005 | Sunaoshi | 700/253 |
| 2003/0168059 A1 | | 9/2003 | Pacey | |
| 2003/0171619 A1 | * | 9/2003 | Perego et al. | 564/331 |
| 2003/0171747 A1 | * | 9/2003 | Kanehira et al. | 606/45 |
| 2007/0265502 A1 | * | 11/2007 | Minosawa et al. | 600/173 |
| 2008/0058602 A1 | * | 3/2008 | Landry | 600/180 |
| 2010/0010313 A1 | * | 1/2010 | Muckner et al. | 600/169 |

FOREIGN PATENT DOCUMENTS

| | | |
|---|---|---|
| JP | 2-257926 | 10/1990 |
| JP | 2002-291684 | 10/2002 |
| JP | 2003-284677 | 10/2003 |
| JP | 2003-334157 | 11/2003 |
| JP | 2005-319101 | 11/2005 |

OTHER PUBLICATIONS

Japanese Official Action dated Apr. 13, 2010.

* cited by examiner

*Primary Examiner* — John P Leubecker
*Assistant Examiner* — Jeffrey H Chang
(74) *Attorney, Agent, or Firm* — Scully, Scott, Murphy & Presser, P.C.

(57) ABSTRACT

An endoscope apparatus of the invention includes an endoscope, camera control unit (CCU), and a trocar. The endoscope includes a heater and a temperature sensor. The CCU is configured to include a resistance value-voltage value conversion section, an analog-digital conversion section, voltage value-temperature table conversion section, a control voltage calculation section, an digital-analog conversion section, a voltage amplification section, a switch control section, and a switch. The trocar 5 includes an insertion detection sensor.

3 Claims, 10 Drawing Sheets

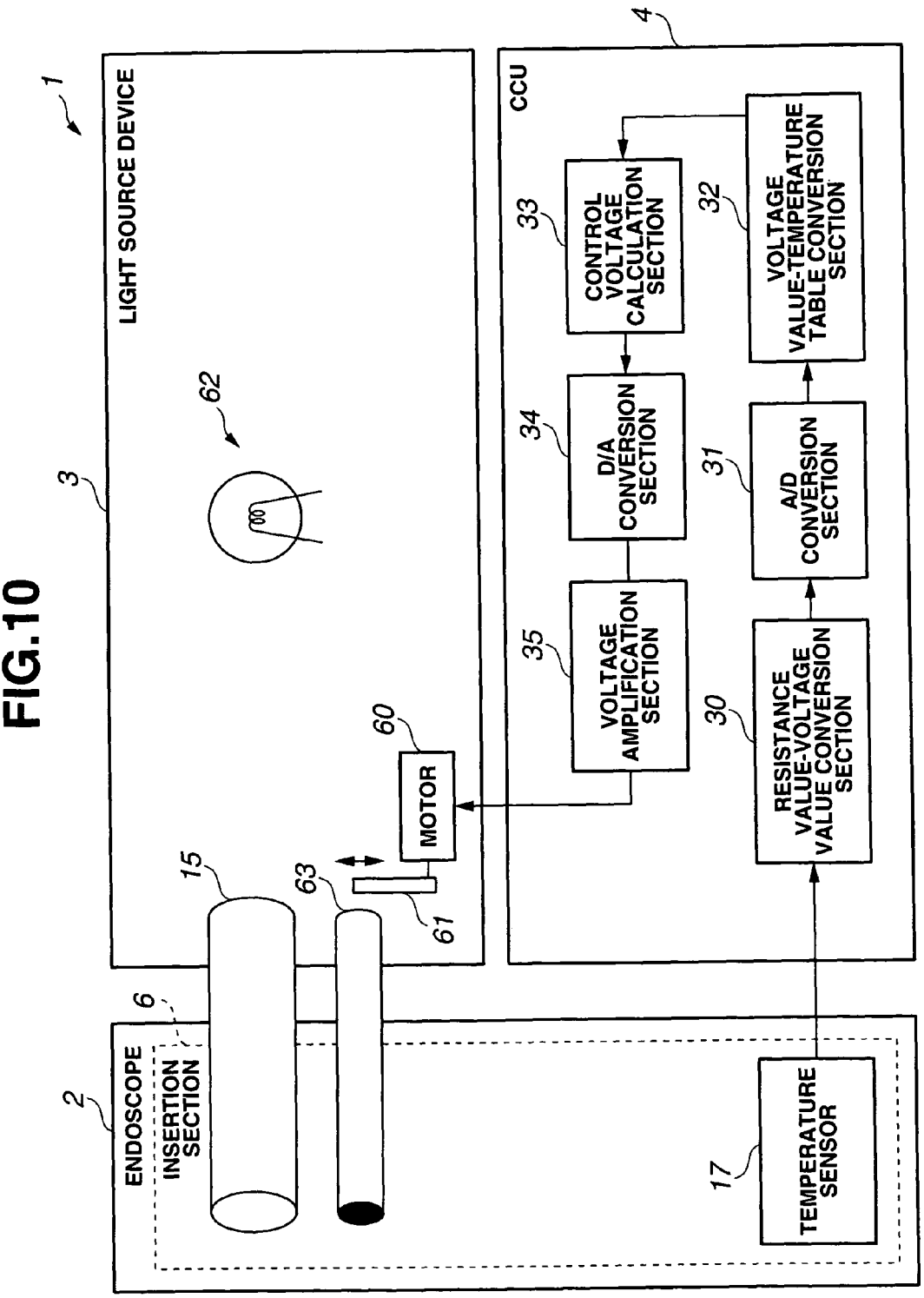

ENDOSCOPE APPARATUS HAVING CONTROLLED HEATER

CROSS REFERENCE TO RELATED APPLICATION

This application claims benefit of Japanese Application No.2005-376237 filed on Dec. 27, 2005, the contents of which are incorporated by this reference.

BACKGROUND OF THE INVENTION

1. Field of the Invention

The present invention relates to an endoscope apparatus capable of preventing fogging of a cover glass.

2. Description of Related Art

In recent years, an endoscope apparatus is used in various fields such as medical field, industrial field, and the like. In the medical field, an endoscope apparatus is used, for example, for observation of organs in a body cavity, therapeutic treatment using a treatment instrument, surgery under observation by an endoscope, and the like.

In such a medical field, an endoscope is inserted into a body, inside environment of which having a temperature equal to a body temperature and high humidity. When an endoscope is inserted in the body having such an environment, fogging sometimes occurs on a cover glass disposed at a distal end portion of the endoscope. In order to prevent the fogging, it is necessary to insert the endoscope into the body after warming the cover glass.

Japanese Unexamined Patent Application Publication No. 2002-291684 proposes a surgical endoscope in which electricity is generated corresponding to a temperature difference between inside and outside of the endoscope, and fogging of a cover glass is prevented by warming the cover glass with a heat generating element disposed at a distal end portion of the endoscope.

SUMMARY OF THE INVENTION

An endoscope apparatus of the present invention is provided with an endoscope including a cover glass at a distal end portion of an insertion section thereof and the endoscope apparatus comprises a heater for warming the cover glass and a heat generation control section for controlling the heater means based on a temperature of the cover glass.

BRIEF DESCRIPTION OF THE DRAWINGS

FIG. 10 is a schematic block configuration diagram of an anti-fogging function according to the third embodiment.

DETAILED DESCRIPTION OF PREFERRED EMBODIMENTS

Hereinafter, detailed description will be made on an endoscope apparatus according to embodiments of the present invention with reference to the drawings. As described above, when performing surgery by using an endoscope apparatus, fogging sometimes occurs on a cover glass disposed at a distal end portion of the insertion section of an endoscope. Therefore, it is necessary to keep the temperature of the cover glass higher than the body temperature but to a degree that heat injury does not occur in a living tissue, that is, for example, from not less than 38° C. to not more than 41° C.

The endoscope system according to the embodiments of the present invention is configured to detect the temperature of the cover glass and control the temperature of the cover glass, thereby preventing the cover glass from fogging and keeping a safe temperature.

First Embodiment

At first, description will be made below on an endoscope apparatus according to the first embodiment with reference to FIG. 1.

Figure 1:
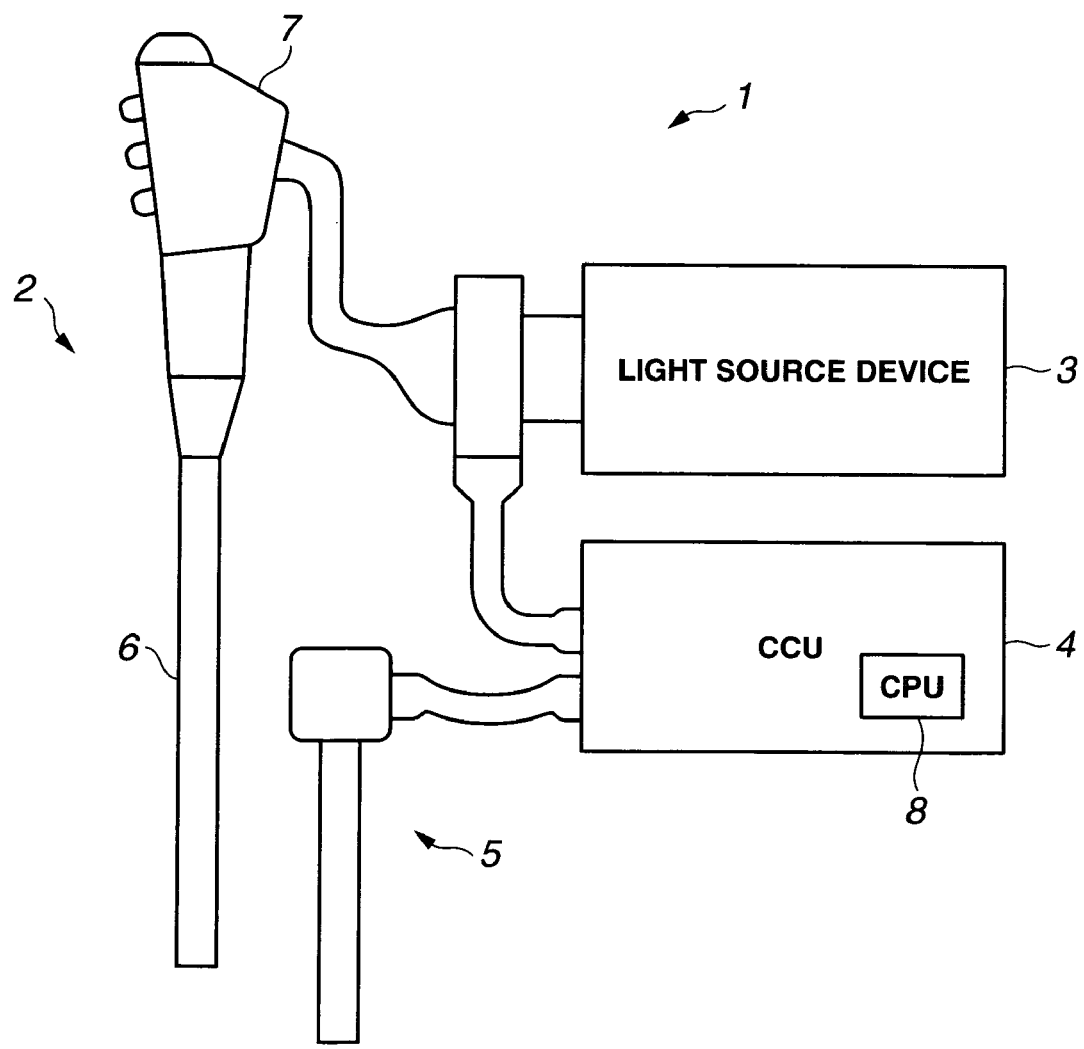
FIG. 1 is a schematic appearance diagram of an endoscope apparatus according to a first embodiment of the present invention.

FIG. 1 is a schematic appearance diagram of the endoscope apparatus. As shown in FIG. 1, an endoscope apparatus 1 includes an endoscope 2, a light source device 3, a camera control unit (hereinafter abbreviated as CCU) 4 serving as a heat generation control section, and a trocar 5.

The endoscope 2 includes an insertion section 6 inserted into a subject to be observed, and an operation section 7 connected to the proximal end of the insertion section 6. The operation section 7 has switches and the like for operating the endoscope 2, and is connected to the light source device 3 and the CCU 4. The trocar 5 is an instrument for inserting the endoscope 2 into an abdominal cavity through an abdominal wall, for example, and is connected with the CCU 4. The CCU 4 has inside thereof various devices including a CPU 8, and various circuits.

An observation using the endoscope apparatus 1 is performed with the trocar 5 disposed so as to pass through an abdominal wall of a human body. The insertion section 6 of the endoscope 2 is inserted into the trocar 5 to be smoothly guided to a desired site to be observed.

The insertion section 6 has a light guide inserted thereto which is described later, so that it is possible to irradiate the site to be observed with the illumination light from the light source device 3. Furthermore, the insertion section 6 has an image-pickup element disposed at the distal end portion thereof, and the image-pickup element captures reflected light from the site to be observed under the control of the CCU4.

In addition, the CCU 4 is operated by various devices including the CPU 8 and the circuits, and processes the captured image. The processed image is outputted and displayed on a monitor and the like not shown, for example.

Next, description will be made on the detailed configuration of the insertion section 6 with reference to FIG. 2.

Figure 2:
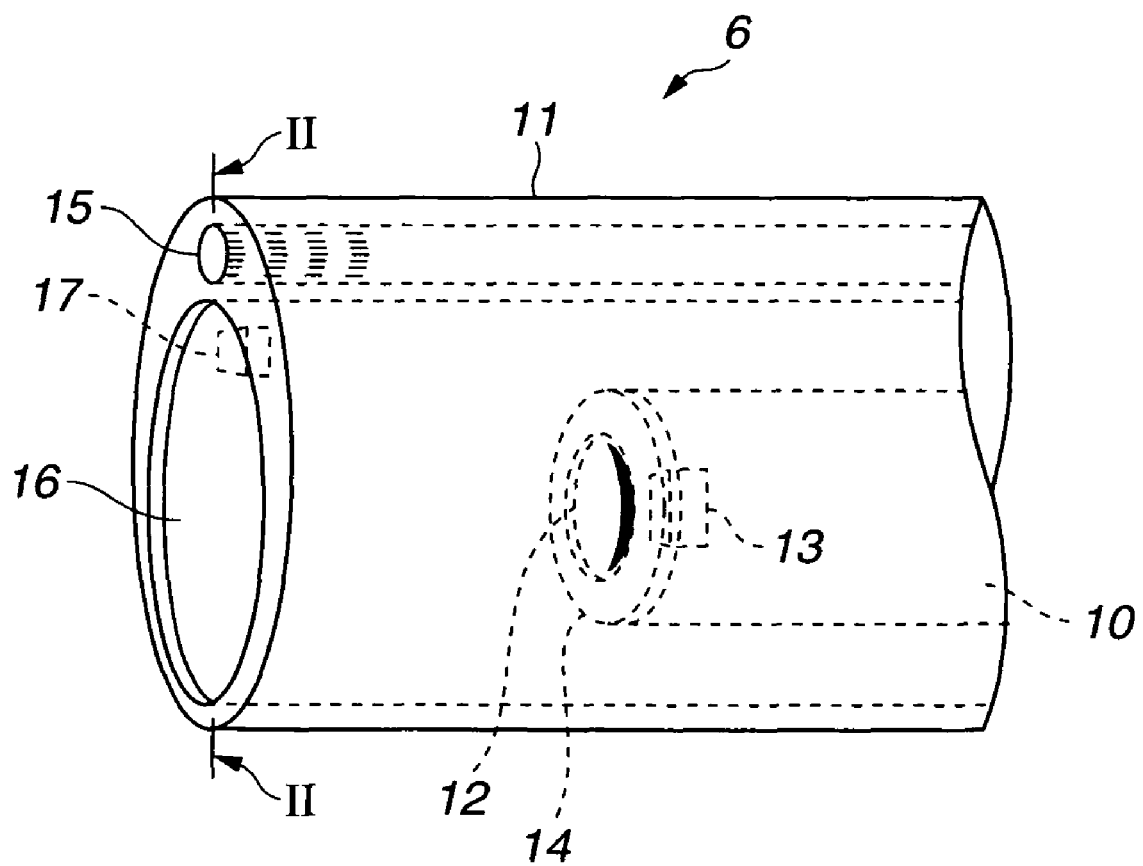
FIG. 2 is a schematic configuration diagram of an insertion section according to the first embodiment.

FIG. 2 is a schematic configuration diagram of the insertion section 6. As shown in FIG. 2, the insertion section 6 includes an inner tube 10 which is a first tube, and an outer tube 11, which is a second tube, having a diameter larger than that of the inner tube 10 and so disposed as to cover the outer circumferential surface of the inner tube 10. Both the inner tube 10 and the outer tube 11 are constituted of an insulation material, since the outer tube 11 has a possibility of directly contacting the living tissue.

In addition, as shown in FIG. 2, the inner tube 10 includes a lens 12, a charge coupled device (hereinafter abbreviated as CCD) 13 serving as image-pickup means, and a heater 14 serving as heat generating means. The heater 14 has a ring shape and disposed such that the outer circumferential surface of the ring shape is along the inner wall surface of the distal end portion of the inner tube 10.

The lens 12 is disposed on the inner circumferential side of the ring-shaped heater 14 located at the distal end portion of the inner tube 10. In addition, the CCD 13 is disposed such that the light-receiving surface thereof is located at a position where the lens 12 image-forms the light from outside in the inside of the inner tube 10.

On the other hand, the outer tube 11 has inside a light guide 15 which is a light guide fiber, inserted thereinto along the axial direction of the outer tube 11, and the distal end of the light guide 15 is exposed on the distal end surface of the outer tube 11. Furthermore, at the distal end portion of the outer tube 11, a disk-shaped cover glass 16 composed of a light-transmitting material is disposed.

A temperature sensor 17 as temperature detection means is so disposed as to contact the inner surface of the cover glass 16 opposite to the lens 12. Note that the cover glass 16 may be composed of a lens. In addition, instead of the light guide 15, a light-emitting diode may be provided at the distal end portion of the insertion section 6.

Below, description will be made on more detailed configuration of the insertion section 6 with reference to a cross-sectional diagram.

Figure 3:
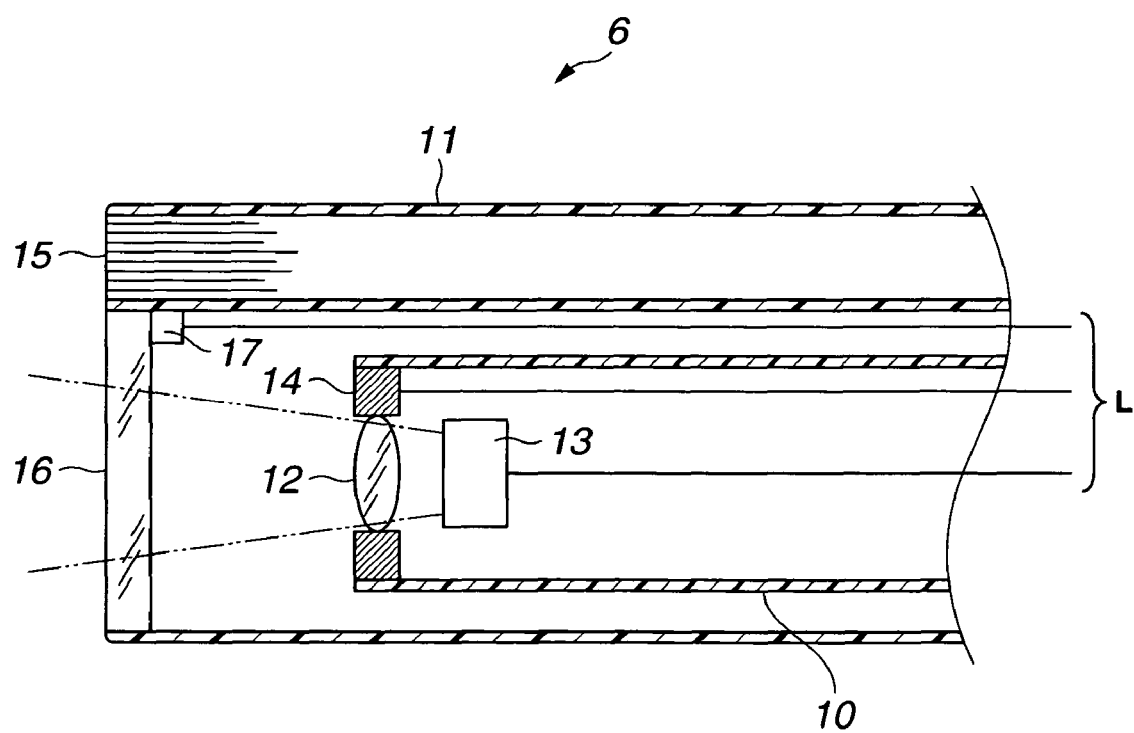
FIG. 3 is a schematic cross-sectional diagram along the II-II line of FIG. 2 according to the first embodiment.

FIG. 3 is a schematic cross-sectional diagram along the II-II line of FIG. 2. As shown in FIG. 3, the CCD 13, the heater 14, and the temperature sensor 17 are each connected to the CCU 4 via a signal line L. The heater 14 and the temperature sensor 17 are each disposed at a position outside of the image-pickup range of the CCD 13 (shown by two-dot chain lines in FIG. 3).

Note that the position and shape of the heater 14 are not limited to those described above. The heater may have any shape and be disposed at any position as long as being disposed at a position between the distal end portion of the inner tube 10 and the opposed surface of the cover glass 16 opposing to the distal end portion so as to be located outside the image-pickup range of the CCD 13.

As described above, the illumination light generated in the light source device 3 is guided by the light guide 15 and irradiated from the distal end of the insertion section 6, that is, the distal end of the outer tube 11. The reflected light from the illuminated site to be observed transmits the cover glass 16 to be image-formed by the lens 12 on the light-receiving surface of the CCD 13. The CCD 13 is controlled by the CCU 4 and picks up the image-formed image to output an image-pickup signal to the CCU4.

In addition, the heater 14 and the temperature sensor 17 are the components for preventing the fogging of the cover glass 16 generated when the insertion section 6 is inserted into a human body. The heater 14 generates heat upon application of voltage from the CCU 4, to warm the cover glass 16.

The temperature of the cover glass 16 is detected by the temperature sensor 17. The resistance value of the temperature sensor 17 changes corresponding to the temperature of the cover glass, and the resistance value is constantly detected by the CCU 4. Then, the CCU 4 controls the voltage to be applied to the heater 14 depending on the detected temperature such that the temperature of the cover glass 16 becomes a predetermined temperature.

Next, description will be made on a configuration of the trocar 5.

Figure 4:
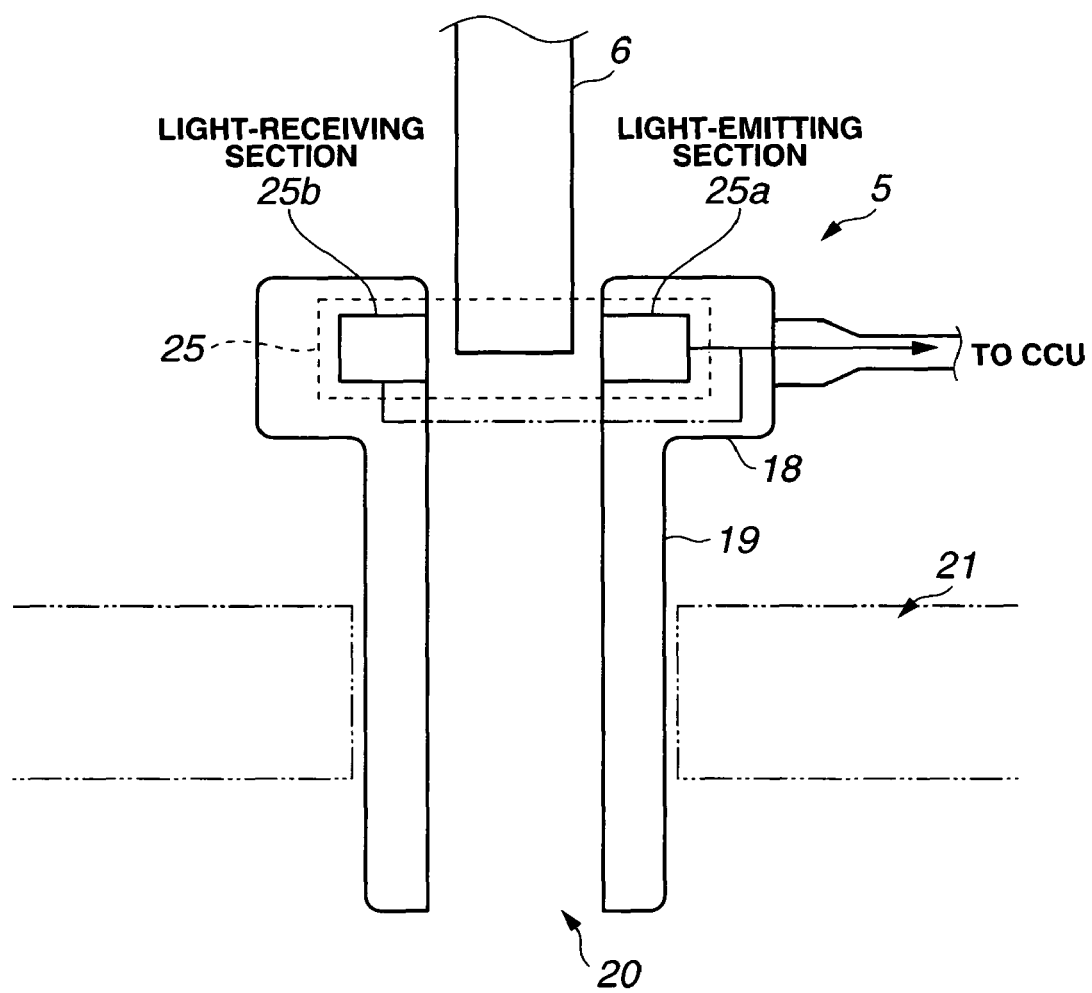
FIG. 4 is a schematic cross-sectional configuration diagram of a trocar according to the first embodiment.

FIG. 4 is a schematic cross-sectional configuration diagram of the trocar 5. The trocar 5 is composed of a main body 18 and an insertion section 19, and has a duct 20, formed in the main body 18 and the insertion section 19, for guiding the insertion section 6 of the endoscope 2. Furthermore, the main body 18 has an insertion detection sensor 25 as insertion detection means for detecting that the insertion section 6 of the endoscope 2 is inserted into the duct 20.

The insertion detection sensor 25 is an insertion sensor which is composed of a photocoupler and the like, for example, and has a light-emitting section 25*a* composed of an LED and the like and a light-receiving section 25*b* composed of a photo transistor, for example, each of which is connected to the CCU 4. Note that the insertion detection sensor 25 may be a sensor such as a contact sensor, for example, if the sensor can detect that the insertion section 6 of the endoscope 2 is inserted into the duct 20.

As described above, in a surgery, the trocar 5 is punctured into a body wall of a living body and used for guiding the instruments such as the endoscope and the treatment instrument into a body cavity. As shown in FIG. 4, the insertion section 6 of the endoscope 2 is inserted into the duct 20 with the insertion section 19 of the trocar 5 being inserted in a body wall 21. When the insertion section 6 of the endoscope 2 is inserted into the duct 20, the light emitted from the light-emitting section 25*a* of the insertion detection sensor 25 is shielded by the insertion section 6.

As a result, the current flowing to the light-receiving section 25*b* changes, so that the insertion detection sensor can detect that the insertion section 6 of the endoscope 2 is inserted into the duct 20. The change of the current is constantly monitored by the CCU 4.

Next, description will be made on an anti-fogging function which is a feature of the endoscope apparatus 1 according to the present embodiment. The function described below is realized by various devices including the CPU 8, and by various circuits.

Figure 5:
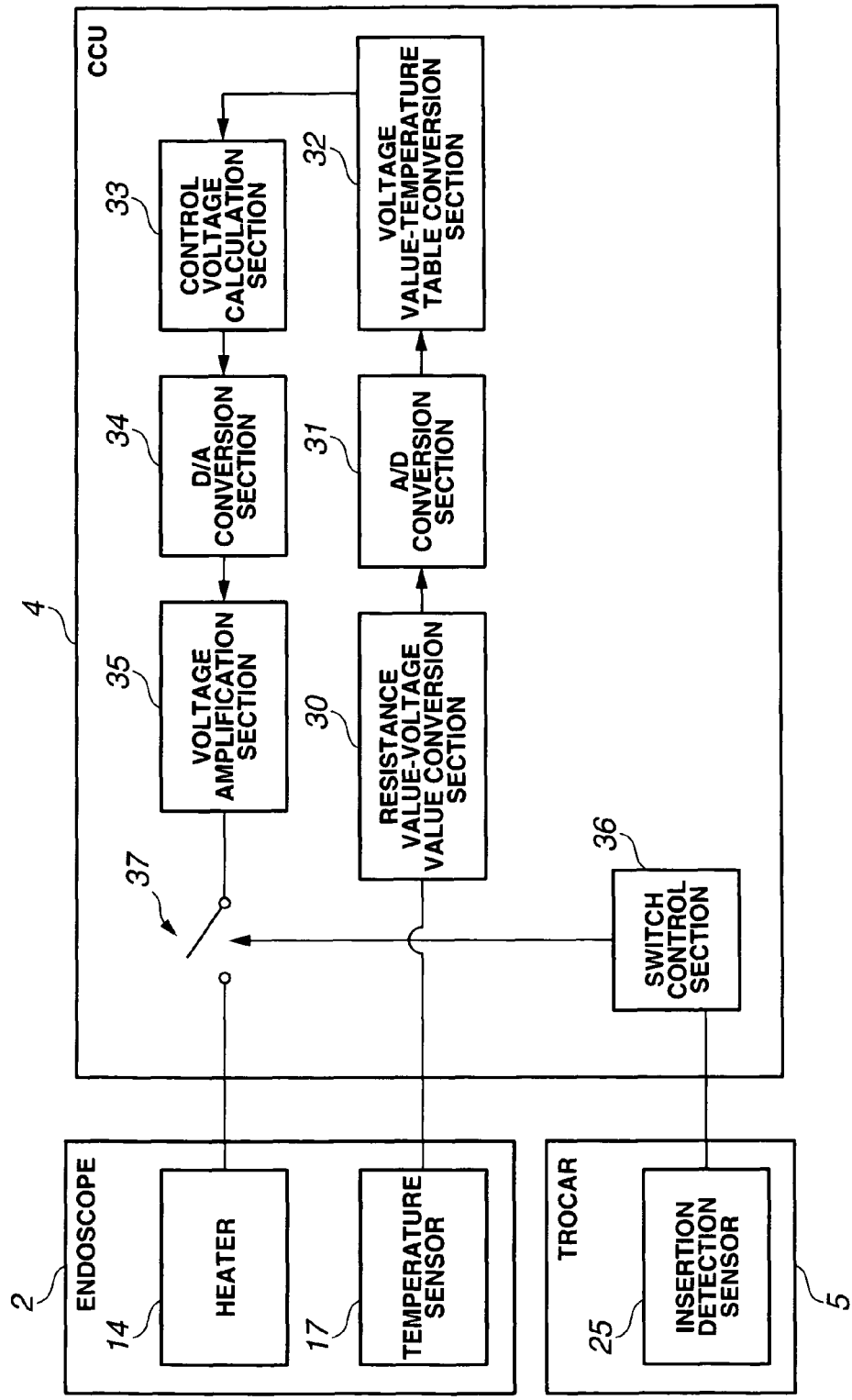
FIG. 5 is a schematic block configuration diagram of an anti-fogging function according to the first embodiment.

FIG. 5 is a schematic block configuration diagram of the anti-fogging function of the endoscope apparatus 1. In FIG. 5, the light source device 3 is not shown and description thereof is omitted. In addition, also as for the CCU 4, description on functions such as image processing generally provided to the endoscope apparatus is omitted.

The endoscope apparatus 1 includes the endoscope 2, the CCU 4, and the trocar 5. The endoscope 2 includes the heater 14 and the temperature sensor 17. The CCU 4 includes a resistance value-voltage value conversion section 30, an analog-digital conversion section (hereinafter abbreviated as an A/D conversion section ) 31, a voltage value-temperature table conversion section 32, a control voltage calculation section 33, a digital-analog conversion section (hereinafter abbreviated as a D/A conversion section) 34, a voltage amplification section 35, a switch control section 36, and a switch 37. The trocar 5 includes the insertion detection sensor 25.

The respective functions of the voltage value-temperature table conversion section 32, the control voltage calculation section 33, and the switch control section 36 are realized by the CPU 8 and the like. The resistance value-voltage value conversion section 30, the A/D conversion section 31, the D/A conversion section 34, the voltage amplification section 35, and the switch 37 are each realized by an electric circuit, or the like.

The temperature sensor 17 is connected with the resistance value-voltage value conversion section 30 via a signal line. The temperature sensor 17, as described above, changes the resistance value thereof corresponding to the temperature of the cover glass 16. The resistance value-voltage value conversion section 30 constantly detects the resistance value of the temperature sensor 17 and converts the detected resistance value into a voltage value.

The voltage value is inputted to the A/D conversion section 31 and converted from an analog signal into a digital signal. The voltage value converted into the digital signal is inputted to the voltage value-temperature table conversion section 32. The voltage value-temperature table conversion section 32 stores in advance table data showing a relationship between the voltage value converted into the digital signal and the temperature. The voltage value-temperature table conversion section 32 calculates the temperature of the cover glass 16 based on the table data and the inputted voltage value. The calculated temperature is inputted to the control voltage calculation section 33.

The control voltage calculation section 33 calculates the voltage value to be applied to the heater 14 based on the inputted temperature such that the temperature of the cover glass 16 becomes a predetermined temperature, for example, a temperature from not less than 38° C. to not more than 41° C. For example, in a case where the temperature of the cover glass 16 is lower than the predetermined temperature and the temperature difference is large, the voltage value to be applied to the heater 14 becomes large. For example, in a case where the temperature of the cover glass 16 is lower than the predetermined temperature and the temperature difference is small, the voltage value to be applied to the heater 14 becomes small. For example, in a case where the temperature of the cover glass 16 is higher than the predetermined temperature, and the temperature difference is large, no voltage is applied to the heater 14. For example, in a case where the temperature of the cover glass 16 is higher than the predetermined temperature, and the temperature difference is small, the voltage value to be applied to the heater 14 becomes small. Note that it may be configured such that the predetermined temperature is freely set by providing a user interface not shown, for example.

The calculated voltage value is inputted to the D/A conversion section 34, and the D/A conversion section 34 converts the inputted voltage value from the digital signal to the analog signal. The converted voltage value is inputted to the voltage amplification section 35 to be amplified.

The voltage amplification section 35 is connected with the heater 14 via the switch 37, and the switch 37 usually becomes on-state when the power source of the CCU 4 is turned on. The voltage amplification section 35 applies the amplified voltage value to the heater 14 via the switch 37.

The insertion detection sensor 25 of the trocar 5 is connected to the switch control section 36 via the signal line. When the insertion detection sensor 25 detects the insertion of the insertion section 6 into the trocar 5, the switch control section 36 turns off the switch 37 for a predetermined time period, that is, sets to zero the voltage value to be applied to the heater 14.

According to the configuration described above, the endoscope apparatus 1 can detect the temperature of the cover glass 16 by the temperature sensor 17 and feed the detected temperature back to the output of the heater 14. As a result, the temperature of the cover glass 16 can be accurately controlled, thereby preventing the fogging of the cover glass 16. The resistance value-voltage value conversion section 30 and the like which are included in the CCU 4 constitute heat generation control means.

Figure 6A:
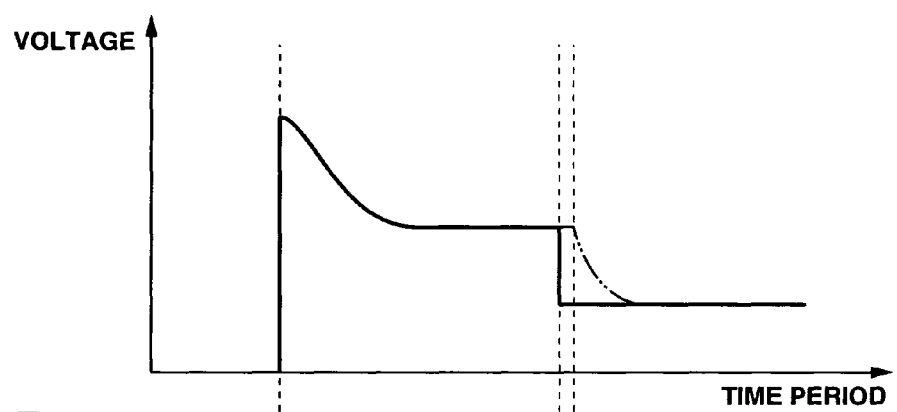
FIG. 6A is a diagram showing a relationship between voltage to be applied to a heater and time period according to the first embodiment.

Next, description will be made on the relationships between the voltage to be applied to the heater 14 and the time period, and the temperature of the cover glass 16 and the time period, with reference to FIGS. 6A and 6B, respectively. FIG. 6A is a diagram showing the relationship between the voltage to be applied to the heater 14 and the time period, and FIG. 6B is a diagram showing the relationship between the temperature of the cover glass 16 and the time period.

A user of the endoscope apparatus 1, in order to prevent the cover glass 16 from fogging, is required to warm the cover glass 16 to a predetermined temperature before inserting the insertion section 6 into a human body as a subject to be observed. In the following description, it is assumed that the predetermined temperature is 39° C., the temperature outside the body, for example, room temperature is 27° C., and the temperature inside the body is 37° C.

Figure 6B:
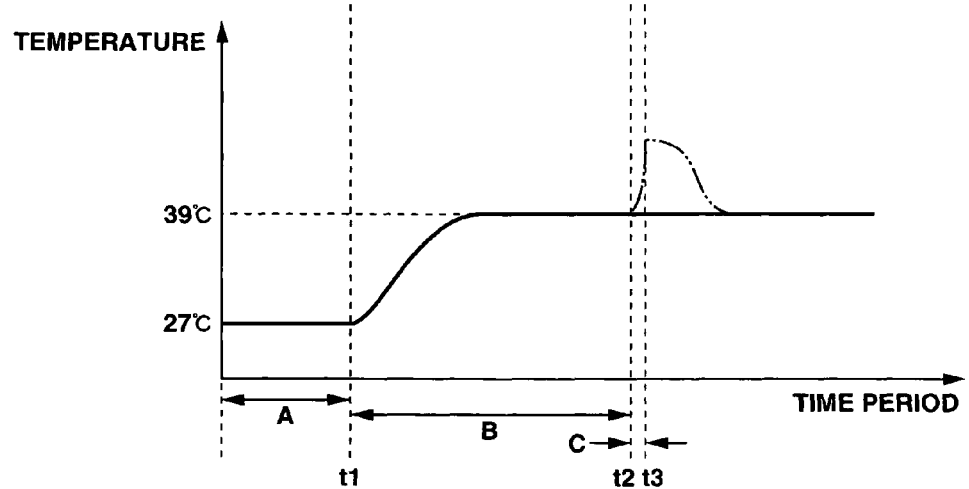
FIG. 6B is a diagram showing a relationship between temperature of a cover glass and time period according to the first embodiment.

At first, before turning on the power source of the endoscope apparatus 1, as shown in the area A in FIGS. 6A and 6B, no voltage is applied to the heater 14 and the temperature of the cover glass 16 is 27° C. which is the same as the room temperature.

The power of the endoscope apparatus 1 is turned on at the time t1, voltage is applied to the heater 14 such that the temperature of the cover glass 16 becomes 39° C. As shown in the area B in FIGS. 6A and 6B, voltage is applied to the heater 14, thereby increasing the temperature of the cover glass 16. With the increase in the temperature of the cover glass 16, voltage to be applied to the heater 14 gradually decreases. The voltage to be applied to the heater 14 is controlled such that the temperature of the cover glass 16 becomes 39° C.

If the insertion section 6 is inserted into the duct 20 of the trocar 5, that is, inside the body, at the time t2, the insertion detection sensor 25 detects that the insertion section 6 is inserted into the duct 20. Then, the switch control section 36 causes the switch 37 to be off-state, and as a result, the voltage applied to the heater 14 becomes zero. At the time t3 after a predetermined time period elapses, the switch control section 36 causes the switch 37 to be on-state again and restarts controlling the voltage to be applied to the heater 14.

Here, description will be made on the reason for providing the time period during which no voltage is applied to the heater 14 in the area C from the time t2 to t3.

The temperature inside the body is 37° C., so that the voltage required to keep the temperature of the cover glass 16 at the predetermined temperature of 39° C. inside the body, is smaller than that required to keep the temperature of the cover glass 16 at the predetermined temperature of 39° C. outside the body. Therefore, immediately after the insertion of the insertion section 6 into the human body, the voltage to be applied to the heater 14 exceeds the voltage required to keep the temperature of the cover glass 16 at 39° C.

As a result, the temperature of the cover glass 16 suddenly increases, thereby causing a possibility of heat injury to the living tissue. FIGS. 6A and 6B show, by the two-dot chain line, the changes of the voltage to be applied to the heater 14 and the temperature of the cover glass 16 in a case where the switch 37 is not turned off in the area C.

As described above, the endoscope apparatus 1 according to the present embodiment detects the temperature of the cover glass 16 by the temperature sensor 17 and feeds the detected temperature back to the output of the heater 14. As a result, the temperature of the cover glass 16 can be accurately controlled, thereby preventing the fogging of the cover glass 16.

In addition, the trocar 5 can prevent the excessive heating of the heater 14 when the insertion section 6 is inserted into the human body, thereby preventing heat injury to the living tissue. Furthermore, it is possible to secure a greater freedom in design of the insertion section of the endoscope of which diameter becomes smaller and smaller in recent years, by disposing the heater 14 in the space from the distal end portion of the inner tube 10 to the opposed surface of the cover glass 16 opposing to the distal end portion of the inner tube.

Second Embodiment Below, the second embodiment will be described in detail by using the drawings.

Because, unlike the configuration of the first embodiment, an endoscope apparatus according to the present embodiment is not provided with the temperature sensor as the temperature detection means, the insertion section can be configured to have a smaller diameter. In addition, the endoscope apparatus according to the present embodiment is provided with identification means for identifying a heater as heat generating means, so that the apparatus can perform accurate temperature control depending on a temperature to resistance value characteristic for each heater.

The present embodiment includes the same configuration of the first embodiment, so that the same components are designated by the same reference numerals and description thereof will be omitted.

At first, description will be made below on an anti-fogging function as a feature of an endoscope apparatus 1 of the present embodiment. The functions described below are realized by various devices including a CPU 8, and by various circuits.

Figure 7:
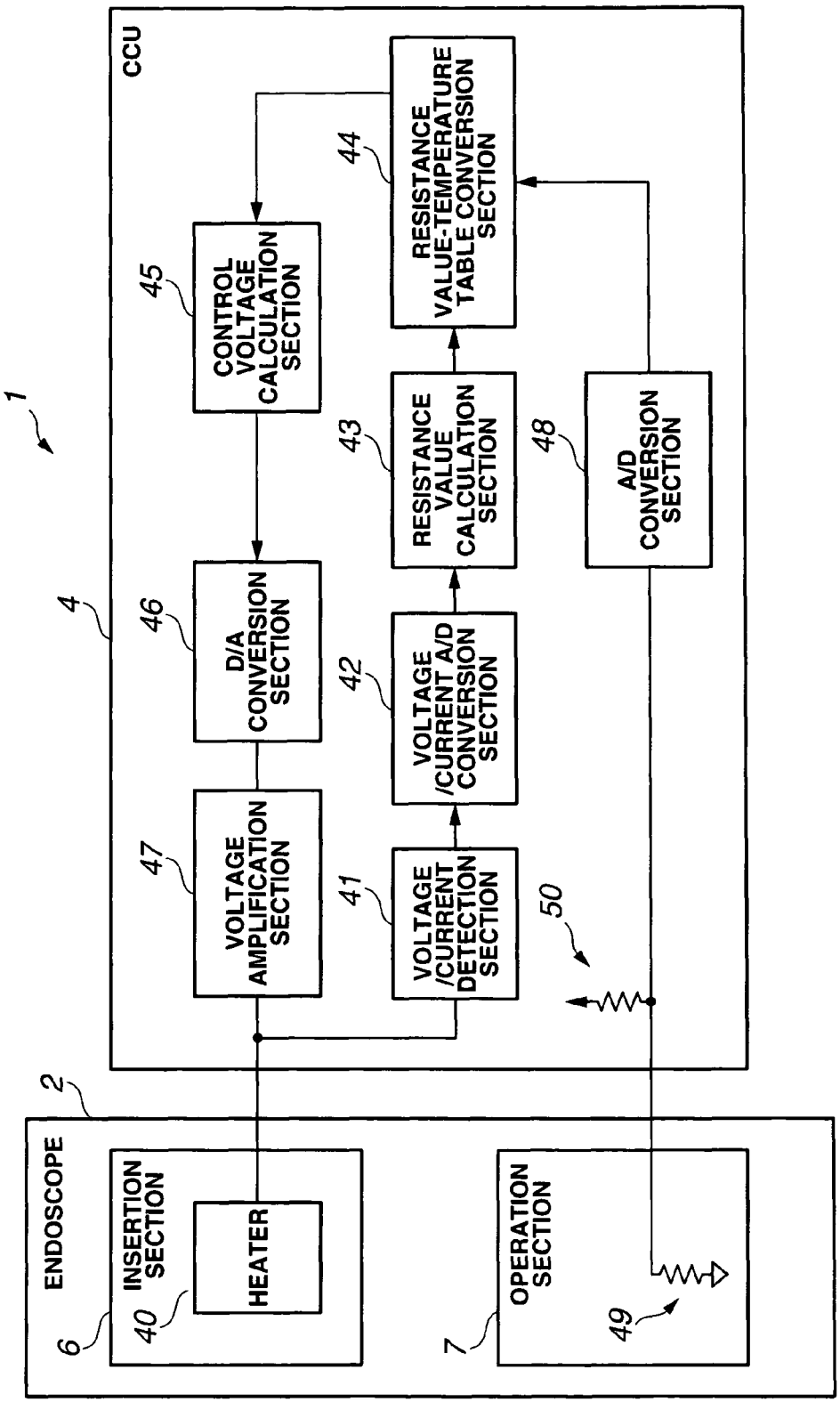
FIG. 7 is a schematic block configuration diagram of an anti-fogging function according to a second embodiment of the present invention.

FIG. 7 is a schematic block diagram of the anti-fogging function of the endoscope apparatus 1. In FIG. 7, same as in the first embodiment, the light source device 3 is not shown and description thereof is omitted. Also as for the CCU 4, description on functions such as image processing generally provided to the endoscope apparatus is omitted.

The endoscope 1 includes an endoscope 2 and a CCU 4 as a heat generation control section. The endoscope 2 includes an insertion section 6 and an operation section 7 provided with a heater 40 as heat generating means and a resistor 49 as identification means, respectively. The CCU 4 includes a voltage/current detection section 41, a voltage/current A/D conversion section 42, a resistance value calculation section 43, a resistance value-temperature table conversion section 44, a control voltage calculation section 45, a D/A conversion section 46, a voltage amplification section 47, an A/D conversion section 48, and a resistor 50.

The respective functions of the resistance value calculation section 43, the resistance value-temperature table conversion section 44, and the control voltage calculation section 45 are realized by the CPU 8 and the like. The voltage/current detection section 41, the voltage/current A/D conversion section 42, the D/A conversion section 46, the voltage amplification section 47, and the A/D conversion section 48 are each realized by an electric circuit, or the like.

The configuration of the distal end portion of the insertion section 6 is similar to that in FIG. 2. The heater 40 in the insertion section 6 includes a heating resistor of which resistance value changes depending on temperature, and the heating resistor is composed of platinum, molybdenum, and the like. The heater 40 has a similar shape as that of the heater 14 (See FIG. 2) according to the first embodiment, and is disposed between the distal end portion of the inner tube 10 and the opposed surface of the cover glass 16 opposing to the distal end portion of the inner tube.

As described above, the resistance value of the heating resistor changes depending on temperature, so that it is possible to control the temperature by controlling the resistance value of the heating resistor. However, the heating resistor has a different temperature to resistance value characteristic depending on the type thereof. Therefore, the calculated temperature of the heating resistor is sometimes different from the actual temperature thereof.

Figure 8:
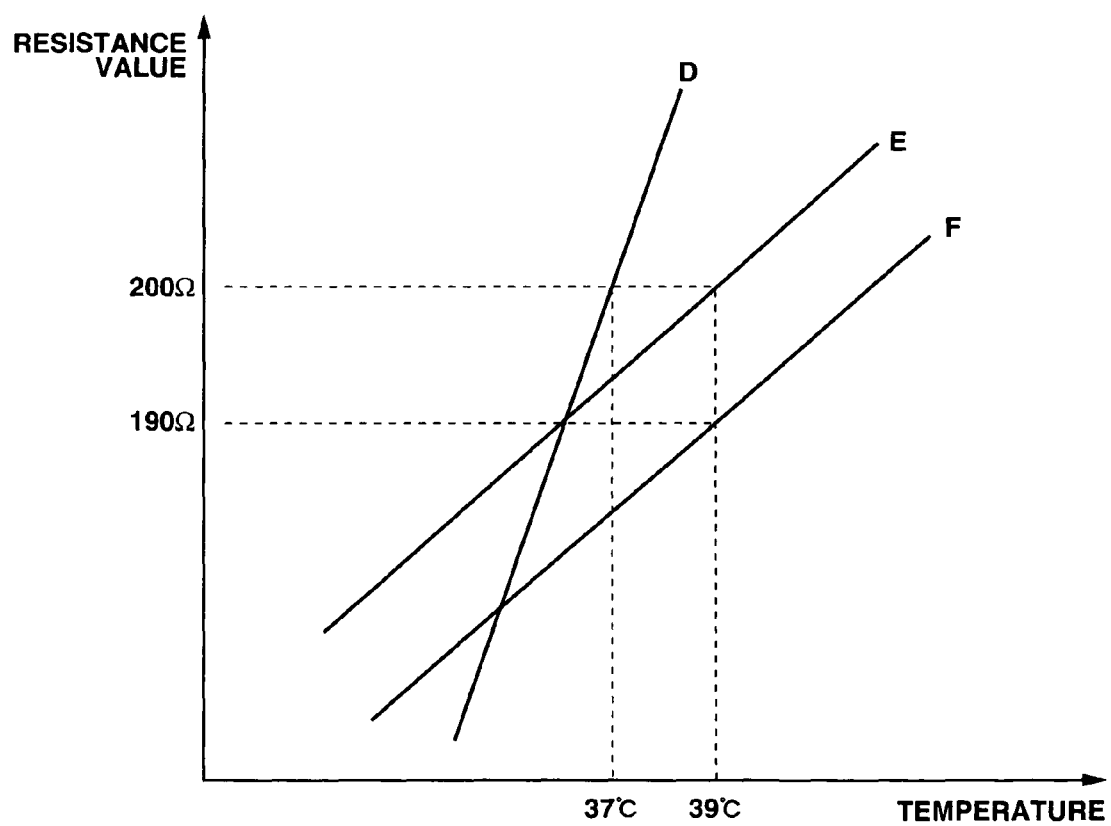
FIG. 8 is an example of a temperature to resistance value characteristic of a heating resistor according to the second embodiment.

FIG. 8 shows an example of the temperature to resistance value characteristic of the heating resistors. FIG. 8 shows the temperature to resistance value characteristics of the heating resistors D, E, and F. As shown in FIG. 8, each of the temperature to resistance value characteristics of the heating resistors D, E, and F has a linear relation, and a different slope and a different intercept.

As a result, if the resistance value of the heating resistor E is controlled to be 200Ω, the temperature thereof becomes 39° C., for example. Meanwhile, if the resistance value of the heating resistor D is controlled to be 200Ω, the temperature thereof becomes 37° C. Therefore, even if the resistance values are controlled to be equal, there is a temperature difference by 2° C. If the desired temperature is 39° C., the resistance value of the heating resistor E is required to be 200 Ω, but the resistance value of the heating resistor F is required to be 190Ω.

Thus, there is a difference in the temperature to resistance value characteristics depending on the type of the heating resistors. Accordingly, it is necessary to take the difference in the characteristics into consideration in order to accurately control the temperature.

Therefore, the operation section 7 includes a resistor 49 having a different resistance value depending on the type of the heater 40 in order to identify the type of the heater 40 determined in advance corresponding to the characteristic of the heating resistor. The CCU 4 can specify the type of the heater 40 by detecting the resistance value of the resistor 49 and calculate the temperature based on the temperature to resistance value characteristic for each type of the heater 40.

The resistor 49 is connected with the A/D conversion section 48 and a resistor 50 having a predetermined resistance value. The A/D conversion section 48 detects a divided voltage generated by applying a predetermined voltage to the resistor 49 and the resistor 50. The resistance value of the resistor 49 can be calculated based on the detected divided voltage, since the resistance value of the resistor 50 is set in advance. In addition, the A/D conversion section 48 converts the calculated resistance value into a digital signal to output the digital signal to the resistance value-temperature table conversion section 44.

On the other hand, the heater 40 is connected to the voltage/current detection section 41 and the voltage amplification section 47 via the signal line. The voltage/current detection section 41 detects the voltage value and current value of the heater 40. The detected voltage value and the current value are inputted to the voltage/current A/D conversion section 42, and the inputted voltage value and the current value are converted from the analog signal to the digital signal in the voltage/current A/D conversion section 42.

The voltage value and current value converted into the digital signal are inputted to the resistance value calculation section 43. The resistance value calculation section 43 calculates the resistance value based on the inputted voltage value and the current value. The calculated resistance value is inputted to the resistance value-temperature table conversion section 44.

The resistance value-temperature conversion section 44 stores in advance table data showing the temperature-voltage value characteristic of the heater 40 corresponding to the resistance value of the resistor 49, and calculates the temperature of the heater based on the inputted resistance value of the resistor 49 and the resistance value of the heater 40.

The control voltage calculating section 45 calculates the voltage value to be applied to the heater 40 based on the inputted temperature such that the temperature of the cover glass 16 becomes the predetermined temperature, for example, the temperature from not less than 38° C. to not more than 41° C. Note that the predetermined temperature may be freely set within the range, from not less than 38° C to not more than 41° C., for example, by providing a user interface not shown.

The calculated voltage value is inputted to the D/A conversion section 46, and the inputted voltage value is converted from the digital signal to the analog signal in the D/A conversion section 46. The converted voltage value is inputted to the voltage amplification section 47 to be amplified. The voltage amplification section 47 applies the amplified voltage value to the heater 40.

According to the above-described configuration, the temperature of the cover glass 16 can be accurately controlled by feeding the temperature of the cover glass 16 to the output of the heater 40, thereby preventing the fogging of the cover glass 16. The voltage/current detection section 41 and the like included in the CCU 4 constitutes heat generation control means.

In addition, the endoscope apparatus 1 according to the present embodiment does not include a temperature sensor 17, so that the insertion section 6 of the endoscope 2 can be configured to have a smaller diameter compared to the first embodiment.

Furthermore, the endoscope apparatus I according to the present embodiment is provided with the resistor 49 as identification means for identifying the heater 40, so that it is possible to accurately control the temperature depending on the type of the heater 40.

Note that the identification means according to the present embodiment is composed of the resistor 49 as the identification circuit element. However, the identification means may be composed of a storage device and the like serving as an identification circuit device for storing the temperature to resistance value characteristic of the heater 40, for example. Furthermore, though the temperature of the heater is calculated by identifying the type of the heater 40 in the present embodiment, the temperature may be calculated by further identifying information on the positional location and the like of the heater 40.

Note that, the endoscope apparatus 1 according to the present embodiment may be configured such that a plurality of the endoscopes 2 each of which has a different type of the heater 40 are connectable to the CCU 4, and the CCU 4 stores the temperature to resistance value characteristic corresponding to each of the endoscopes 2.

Furthermore, though the resistance value-temperature table conversion section 44 stores in advance the temperature to resistance value characteristic corresponding to the type of the heater 40 in the present embodiment, the section may store in advance the temperature to resistance value characteristic for individual heating resistor constituting the heater 40. This enables more precise temperature control to be performed.

Note that the endoscope apparatus 1 of the present embodiment may include the trocar 5 likewise with the configuration in the first embodiment. With this configuration, it is possible to prevent excessive heating of the heater 40 when the insertion section 6 is inserted into a human body, thus preventing heat injury to the living tissue.

Third Embodiment

Below, detailed description will be made on the third embodiment with reference to the drawings.

Unlike the first embodiment, an endoscope apparatus of the present embodiment is not provided with a heater, and heat generating means is composed of a light guide. The heater is required to have a heat capacity enough to heat the cover glass, so that the size of the element is larger than that of the temperature sensor, for example. Therefore, in the present embodiment, the insertion section can be configured to have a smaller diameter compared to the first embodiment.

The present embodiment includes the same configuration as that in the first embodiment, so that the same components are designated by the same reference numerals and description thereof will be omitted.

Figure 9:
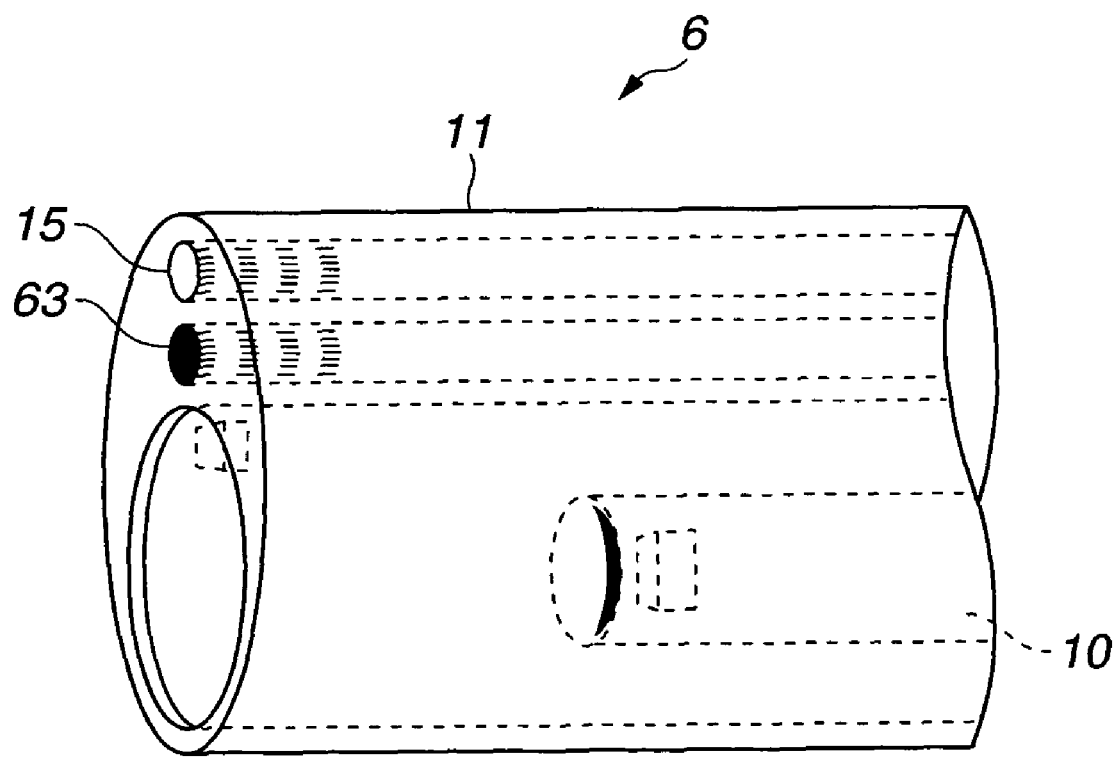
FIG. 9 is a schematic configuration diagram showing an insertion section according to a third embodiment of the present invention.

FIG. 9 is a schematic configuration diagram of an insertion section 6. As shown in FIG. 9, unlike the first embodiment, an inner tube 10 is not provided with the heater 14. An outer tube 11 has a light guide 15 and a light guide 63 having a light-shielded distal end surface, inserted along the axial direction of the tube. Illumination light enters the light guide 63 to be changed into heat on the distal end surface thereof.

That is, the light guide 63 constitutes heat generating means and has a function similar to that of the heater 14 in the first embodiment. The heating amount of the light guide 63 is changed by controlling the light amount of the illumination light entering the light guide 63 in a light source device 3. The control of the heating amount of the light guide 63 will be described later.

Next, description will be made on a general configuration of an anti-fogging function of an endoscope apparatus 1 according to the present embodiment. The functions described below are realized by various devices including a CPU 8, and by various circuits. FIG. 10 is a schematic block diagram of the anti-fogging function of the endoscope apparatus 1. As for a CCU 4, description on functions such as image processing generally provided to the endoscope apparatus is omitted.

The endoscope apparatus 1 includes an endoscope 2, the light source device 3, and the CCU 4. The light source device 3 and the CCU 4 constitute a heat generation control section. The endoscope 2 includes the insertion section 6 provided with a temperature sensor 17 as temperature detection means. The light source device 3 includes a motor 60, a light-shielding plate 61, and a lamp 62. In addition, the light guides 15, 63 are provided so as to extend from the light source device 3 to the distal end portion of the insertion section 6. The CCU 4 includes a resistance value-voltage value conversion section 30, an A/D conversion section 31, a voltage value-temperature table conversion section 32, a control voltage calculation section 33, a D/A conversion section 34, and a voltage amplification section 35.

The respective functions of the voltage value-temperature table conversion section 32 and the control voltage calculation section 33 are realized by the CPU 8 and the like. In addition, the resistance value-voltage value conversion section 30, the A/D conversion section 31, the D/A conversion section 34, and the voltage amplification section 35 are each realized by an electric circuit, or the like.

The temperature sensor 17 is connected with the resistance value-voltage value conversion section 30 via a signal line. As described above, the temperature sensor 17 changes the resistance value thereof depending on the temperature of the cover glass 16. The resistance value-voltage value conversion section 30 constantly detects the resistance value of the temperature sensor 17, and converts the detected resistance value into a voltage value.

The voltage value is inputted to the A/D conversion section 31 and converted from the analog signal to the digital signal. The voltage value converted into the digital signal is inputted into the voltage value-temperature table conversion section 32. The voltage value-temperature table conversion section 32 stores in advance table data showing the relationship between the voltage value converted into the digital signal and the temperature. The voltage value-temperature table conversion section 32 calculates the temperature of the cover glass 16 based on the table data and the inputted voltage value. The calculated temperature is inputted to the control voltage calculation section 33.

The control voltage calculation section 33 calculates the voltage value to be applied to the motor 60 based on the inputted temperature. The calculated voltage value is inputted to the D/A conversion section 34, and the inputted voltage value is converted from the analog signal to the digital signal in the D/A conversion section 34. The converted voltage value is inputted to the voltage amplification section 35 to be amplified.

The voltage amplification section 35 is connected to the motor 60 and applies the amplified voltage to the motor 60. The motor 60 causes the light-shielding plate 61 to operate depending on the applied voltage. The light-shielding plate 61 is so disposed as to adjust the illumination light entering the light guide 63 depending on the voltage applied to the motor 60.

When the power source of the endoscope apparatus 1 is turned on, the lamp 62 is lighted, and the illumination light enters the light guides 15 and 63. The illumination light entered the light guide 63 is shielded on the distal end surface of the insertion section 6 to generate heat. The generated heat warms the cover glass 16 and prevents the cover glass 16 from fogging.

The temperature sensor 17 detects the temperature of the cover glass 16, and the light-shielding plate operates depending on the detected temperature. As a result, the light amount of the illumination light entering the light guide 63 is adjusted, so that the temperature of the cover glass is controlled.

As described above, the endoscope apparatus 1 according to the present embodiment detects the temperature of the cover glass 16 by the temperature sensor 17 to feed the detected temperature back to the heat generation by the light guide 63. As a result, the temperature of the cover glass 16 can be controlled accurately, thereby preventing the cover glass from fogging. The resistance value-voltage value conversion section 30 and the like included in the CCU 4 constitute the heat generation control means.

In addition, the insertion section 6 is not provided with a heater as the heat generating means, so that the insertion section of the endoscope can be configured to have a smaller diameter.

Note that, also in the present embodiment, the endoscope apparatus I may be configured to include the trocar 5 likewise with the first embodiment. With the configuration, it is possible to prevent excessive heating of the heater 40 when the insertion section 6 is inserted into a human body, thus preventing heat injury to the living tissue.

As described above, the endoscope apparatus according to the present embodiment is capable of accurately controlling the temperature of the distal end portion of the endoscope and preventing the fogging of the cover glass.

Note that the present invention is not limited to the above-described embodiments, and modification could be made without departing from the scope of the invention.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An endoscope apparatus comprising:
   an endoscope comprising:
      an insertion section comprising a first tube and a second tube having a diameter larger than a diameter of the first tube, the second tube being disposed so as to cover an outer circumferential surface of the first tube;
      a cover glass disposed at a distal end portion of the second tube;
      a heating resistor adapted to heat the cover glass by resistance heating, the heating resistor having a controllable resistance value and a predetermined temperature to resistance value characteristic; and
      an identification circuit element adapted to identify the predetermined temperature to resistance value characteristic of the heating resistor; and
   a heat generation control section adapted:
      to be detachably connected to the endoscope,
      to receive a target temperature,
      to determine a resistance value associated with the target temperature based on the predetermined temperature to resistance value characteristic of the heating resistor identified by the identification circuit element provided in the connected endoscope, and
      to control the resistance value of the heating resistor based on the determined resistance value.

2. The endoscope apparatus according to claim 1, wherein the heat generation control section suspends heating by the heating resistor for a predetermined time period in a case where the insertion section is inserted into a trocar for guiding insertion of the endoscope into a body cavity.

3. The endoscope apparatus according to claim 2, wherein the trocar includes an insertion sensor for detecting whether or not the insertion section is inserted into the trocar, and the heat generation control section is adapted to suspend heating by the heating resistor based on a detection result by the insertion sensor.

* * * * *